United States Patent
Kim et al.

(10) Patent No.: US 12,087,025 B2
(45) Date of Patent: Sep. 10, 2024

(54) DEVICE FOR GENERATING DATA FOR ART-BASED PSYCHOANALYSIS AND METHOD FOR AUGMENTATION AND EFFICIENT MANAGEMENT OF DATA FOR ART-BASED PSYCHOANALYSIS USING THE SAME

(71) Applicant: i-Scream arts Co., Ltd., Seoul (KR)

(72) Inventors: Ji-hoon Kim, Seoul (KR); Ki-seok Park, Seoul (KR)

(73) Assignee: i-Scream arts Co., Ltd., Seoul (KR)

( * ) Notice: Subject to any disclaimer, the term of this patent is extended or adjusted under 35 U.S.C. 154(b) by 22 days.

(21) Appl. No.: 17/916,245

(22) PCT Filed: Nov. 16, 2021

(86) PCT No.: PCT/KR2021/016748
§ 371 (c)(1),
(2) Date: Sep. 30, 2022

(87) PCT Pub. No.: WO2023/033241
PCT Pub. Date: Mar. 9, 2023

(65) Prior Publication Data
US 2023/0326089 A1 Oct. 12, 2023

(30) Foreign Application Priority Data

Sep. 3, 2021 (KR) .................. 10-2021-0117708
Nov. 11, 2021 (KR) .................. 10-2021-0154397

(51) Int. Cl.
*G06T 9/00* (2006.01)
*A61B 5/00* (2006.01)
*A61B 5/16* (2006.01)
*G06T 11/20* (2006.01)

(52) U.S. Cl.
CPC .............. *G06T 9/002* (2013.01); *A61B 5/165* (2013.01); *G06T 11/203* (2013.01);
(Continued)

(58) Field of Classification Search
CPC ... G06T 9/002; G06T 11/203; G06T 2200/24; G06T 2210/22; A61B 5/165; A61B 5/7264
See application file for complete search history.

(56) References Cited

U.S. PATENT DOCUMENTS 10,402,061 B2 * 9/2019 Kohlmeier ............ G06F 3/0482
2010/0054535 A1 * 3/2010 Brown .................. G06V 10/235
382/103
(Continued)

FOREIGN PATENT DOCUMENTS

KR 100750871 B1 8/2007
KR 20180108288 A 10/2018
(Continued)

OTHER PUBLICATIONS

Kim, Su-Kyung et al., "Development of Fuzzy Reasoning based Psychological Diagnosis Application with Automatic Hand-drawing Analysis", Journal of Digital Contents Society, vol. 22, No. 3, pp. 519-525, 2021.

*Primary Examiner* — YuJang Tswei
(74) *Attorney, Agent, or Firm* — NKL LAW; Jae Youn Kim

(57) ABSTRACT

A device for generating data for art-based psychoanalysis according to one embodiment of the present disclosure may include: a user interface which provides a user, i.e., an examinee with an interactive environment; a first drawing analysis part which is subjected to learning using a first artificial intelligence model, analyzes drawing data which the user input through the user interface to crop regional data of interest from the drawing data, and compresses the data of a region of interest or uncompresses the compressed data of a region of interest to restore the drawing data; a storing part which stores labeling information of the size, location and angle of an object included in the compressed data of a
(Continued)

region of interest; and a second drawing analysis equipped with a second artificial intelligence model that partially augments an object of an art-based psychoanalytic element included in the drawing data, followed by learning.

9 Claims, 7 Drawing Sheets

(52) U.S. Cl.
CPC ......... *A61B 5/7264* (2013.01); *G06T 2200/24* (2013.01); *G06T 2210/22* (2013.01)

(56) References Cited

U.S. PATENT DOCUMENTS

| | | | | |
|---|---|---|---|---|
| 2012/0116186 | A1* | 5/2012 | Shrivastav | G10L 25/48 600/301 |
| 2016/0191995 | A1* | 6/2016 | el Kaliouby | H04N 21/812 725/12 |
| 2017/0171614 | A1* | 6/2017 | el Kaliouby | G16H 50/70 |
| 2019/0012592 | A1* | 1/2019 | Beser | G06N 3/063 |
| 2019/0025400 | A1* | 1/2019 | Venalainen | G06N 20/00 |
| 2021/0004589 | A1* | 1/2021 | Turkelson | G06V 30/19173 |
| 2021/0177295 | A1* | 6/2021 | Maximo | G06T 7/0012 |
| 2021/0383281 | A1* | 12/2021 | Seimasa | G06N 3/08 |
| 2021/0406679 | A1* | 12/2021 | Wen | G06V 20/56 |
| 2022/0292331 | A1* | 9/2022 | Zimmermann | G06N 3/045 |
| 2022/0351730 | A1* | 11/2022 | Yang | G06Q 30/0201 |
| 2023/0081601 | A1* | 3/2023 | Wang | G06V 10/25 378/96 |

FOREIGN PATENT DOCUMENTS

| | | | |
|---|---|---|---|
| KR | 20200084444 A | 7/2020 | |
| KR | 20200090021 A | 7/2020 | |

* cited by examiner

DEVICE FOR GENERATING DATA FOR ART-BASED PSYCHOANALYSIS AND METHOD FOR AUGMENTATION AND EFFICIENT MANAGEMENT OF DATA FOR ART-BASED PSYCHOANALYSIS USING THE SAME

TECHNICAL FIELD

The present disclosure relates to a device for generating data for art-based psychoanalysis and a method for augmentation and efficient management of data for art-based psychoanalysis using the same In particular, the present disclosure relates to a technology which increases cleansing and a compression rate of drawing data by focusing on a significant region of interest (ROI) in conformity with art-based psychoanalysis with an auto-encoder, and which partially augments an art-based psychoanalytic element from the drawing data using a GNA (Generative Adversarial Network), allowing learning an artificial intelligence model for psychoanalysis.

BACKGROUND TECHNOLOGY

According to the prior art, in order to efficiently store data in the storage space, provided is an autoencoder using a data compression manner and a deep learning technique. The autoencoder is divided into an encoder part and a decoder part, wherein the encoder transforms a value into a feature level by embedding an original image into a certain feature domain, and the decoder refers to a part for uncompressing (restoring) a feature level into an original image. Studies for these encoder and decoder as a neural network using deep learning are in progress.

As considering the feature of an image for an art-based psychological test, when applying an original image to the autoencoder, there is a problem that a large amount of insignificant information exists as compared to necessary information for an actual art-based psychological test. For example, when drawing a house during a HTP test, an original image includes an unnecessarily large amount of blankness besides information needed for art-based psychological test, but this blankness not affecting any result of art-based psychological test. The number of windows is a critical element that affects a result of art-based psychological test. However, detailed parts of a window, such as a form and a shape thereof, are not such elements greatly influence the result.

Further, when applying an original image to the autoincoder, such unnecessary parts are also supposed to be uncompressed and thus the extent of feature transformation becomes voluminous proportional to the quantity of unnecessary information, consequently occurring a problem resulting in poor compression efficiency according to thereto.

Meanwhile, when performing learning an artificial intelligence model with a restricted learning data, an augmentation technique is generally used for increasing learning performance through regularization of the artificial intelligence model. Such an augmentation technique includes geometry distortion, photometric distortion, GAN augmentation, a combination of different images, etc.

In the aforementioned augmentation techniques, the GAN augmentation generates a new image that did not exist before, without foreignness with an existing image form by using deep learning that generates an image similar to an actual image for a certain class, i.e., a GAN (Generative Adversarial Network), and augments data for learning, thus increasing performance of the artificial intelligence model.

When generating data using a prior GAN, the most important aim is to generate images of the same class without foreignness. However, in the art-based psychological test, it is more important whether a psychoanalytic element exists or not and how a drawing was drawn than generating images of the same class without liability of foreignness and thus it is difficult that the prior GAN generates data along with giving a precise difference to an element by each psychoanalytic element. Further, when generating images at random, it is involved to achieve an additional labeling work for generated images, incurring the increase in expenses.

DISCLOSURE OF THE INVENTION IN DETAIL

Technical Problem

The present disclosure aims to provide a device for generating data for art-based psychoanalysis, which improves a compression rate of drawing data by breaking down significant data of a region of interest according to art-based psychoanalysis with an autoincoder, followed by compression, allowing efficiently storing data in a storing part with a limited storage capacity, and also to provide a method for augmentation and efficient management of data for art-based psychoanalysis using the same.

Further, the present disclosure aims to provide a device for generating data for art-based psychanalysis, which partially augments an object of a psychoanalytic element included in drawing data through a partial GAN (Generative Adversarial Network) and learns an artificial intelligence model for art-based psychoanalysis as inputting labeling information of the size, location and angle of the object, allowing reducing expenses for a labeling work, and also to provide a method for augment and efficient management of data for art-based psychoanalysis using the same.

Further, the present disclosure aims to provide a device for generating data for art-based psychoanalysis, which is capable of deducing diverse results of art-based psychoanalysis from drawing data through a combination of partial GNAs, and also to provide a method for augmentation and efficient management of data for art-based psychoanalysis using the same.

However, technical solutions to be achieved by the present disclosure are not limited to the aforementioned solutions, and other not-mentioned technical solutions may be clearly understood by the skilled person in the art to which the present disclosure pertains from the description below.

Technical Solutions

In order to achieve aims as described above, a device for generating data for art-based psychoanalysis according to one embodiment of the present disclosure may include: a user interface that provides a user, i.e., an examinee with an interactive environment; a first drawing analysis part that is subjected to learning using a first artificial intelligence model, analyzes drawing data that was input through the user interface by the user to crop data of a region of interest from the drawing data, and compresses the data of a region of interest or uncompresses compressed data of a region of interest to restore the drawing data; a storing part that stores labeling information of a size, a location and an angle of an object included in the compressed data of a region of interest; and a second drawing analysis part that is equipped with a second artificial intelligence model which partially augments an object of an art-based psychoanalytic element included in the drawing data, followed by learning.

Further, the first artificial intelligence model may be an autoencoder for compressing or uncompressing the data of a region of interest.

Further, the first drawing analysis part may crop data of a region of interest from the drawing data, and then normalize the data of a region of interest into a preset size, followed by encoding normalized data of a region of interest to compress feature information.

Further, the feature information may be labeling information of a size, a location and an angle of an object included in the data of a region of interest.

Further, the first drawing analysis part may decode the feature information to uncompress compressed normalized data of a region of interest, regulate a size of an object included in the normalized data of a region of interest through size information to restore the object so as to make the size thereof become the same as that of an object of the drawing data, and identify a location of an object included in the normalized data of a region of interest through location information, followed by regulating the location of the object to the same location as that of an object of the drawing data to restore the drawing data.

Further, the second artificial intelligence model may be a partial GAN (Generative Adversarial Network) for partially augmenting an object included in normalized data of a region of interest which is uncompressed through decoding of the feature information.

Further, a plurality of the partial GANs may be equipped in the second drawing analysis part to partially augment the object and subjected to learning through feedback on partial augmentation of the object, and generate data for art-based psychoanalysis with the partial augmentation of the object.

Further, the device for generating data for art-based psychoanalysis may further include: a database in which art-based psychoanalytic information is pre-stored; a psychological state analysis part that is subjected to learning using a third artificial intelligence model and analyzes the data for art-based psychoanalysis and the art-based psychoanalytic information to firstly deduce psychological state information of the user; and a communication part for communicating with a terminal of a second user, i.e., a drawing analyst.

Further, the terminal of the second user may provide the second user with drawing data which the user inputs into the user interface, and be equipped with a second user interface so as to input additional information including a psychoanalytic opinion on the drawing data analyzed by the second user.

Further, the psychological state analysis part may add the additional information to the psychological state information of the user firstly deduced through analyzing the data for art-based psychoanalysis and the art-based psychoanalytic information to secondly deduce psychological state information of the user.

A method for augmentation and efficient management of data for art-based psychoanalysis according to one embodiment of the present disclosure may include steps of: subjecting a first drawing analysis part to learning using a first artificial intelligence model, a second drawing analysis part using a second artificial intelligence part and a psychological state analysis part using a third artificial intelligence model; cropping data of a region of interest from drawing data that was input through a user interface by a user and compressing the data of a region of interest, by the first drawing analysis part; storing labeling information of a size, a location and an angle of an object included in compressed data of a region of interest in a storing part; uncompressing the compressed data of a region of interest through feature information and then restoring the drawing data, by the first drawing analysis part; and partially augmenting and learning objects of an based psychoanalytic element included in the drawing data and generating data for art-based psychoanalysis through a combination of the objects, by the second drawing analysis part.

Further, the method for augmentation and efficient management of data for art-based psychoanalysis according to one embodiment of the present disclosure may further include steps of: firstly deducing psychological state information of the user by analyzing the data for art-based psychoanalysis and art-based psychoanalytic information pre-stored in a database by the psychological state analysis part; receiving drawing data of the user through a second user interface equipped in a terminal of a second user, i.e., a psychoanalyst, and a communication part; inputting additional information including a psychoanalytic opinion on the drawing data into the second user interface, following analyzing the drawing data by the second user; secondly deducing psychological state information of the user by adding, to the psychological state information of the user deduced by the first psychological state analysis part, the additional information received through the communication part; and providing the user with the firstly or secondly deduced psychological state information of the user through the user interface.

A computer program may be provided, which stored in a computer-readable recording medium to perform the method for augmentation and efficient management of data for art-based psychoanalysis according to embodiments of the present disclosure.

Advantageous Effect

The present disclosure is capable of improving a compression rate of drawing data efficiently storing data in a storing part with a limited storage capacity by compressing data of a region of interest to be used for art-based psychoanalysis in drawing data rather than storing the drawing data in a storing part as it is.

Further, the present disclosure is capable of reducing expenses for a labeling work by partially augmenting an object of a psychoanalytic element included in drawing data through a partial GAN (Generative Adversarial Network) and inputting labeling information of the size, location and angle of the objects.

Further, the present disclosure is capable of deducing diverse results of art-based psychoanalysis from drawing data through a combination of partial GNAs.

However, advantageous effects to be obtained by the present disclosure are not limited to the aforementioned effects, and other not-mentioned advantageous effects may be clearly understood by the skilled person in the art to which the present disclosure pertains from the description below.

BEST MODE OF THE INVENTION

Figure 1:
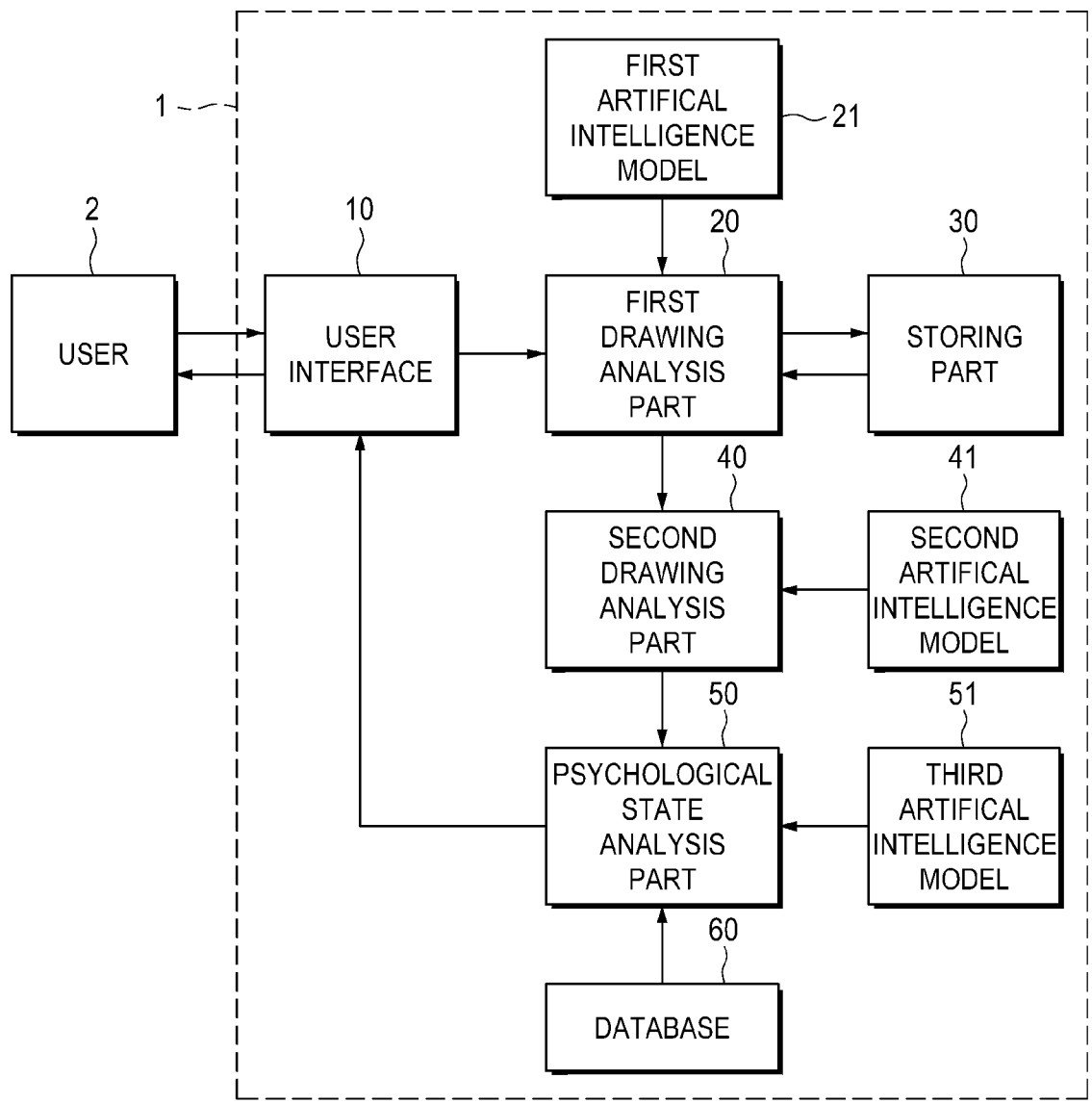
FIG. 1 is a block view schematically showing a device for generating data for art-based psychoanalysis according to one embodiment of the present disclosure.

Hereinafter, exemplary embodiments of the present disclosure will be described in detail so as to be easily implemented by the skilled person in the art, with reference to the accompanying drawings. A description of the present disclosure is merely an exemplary embodiment for a structural or functional description and the scope of the present disclosure should not be construed as being limited by exemplary embodiments described in a text. That is, since the exemplary embodiment can be variously changed and have various forms, the scope of the present disclosure should be understood to include equivalents capable of realizing the technical spirit. Further, it should be understood that since a specific exemplary embodiment should not include all objects or effects or include only the effect, the scope of the present disclosure is not limited by the object or effect.

Meanings of terms described in the present disclosure should be understood as follows.

The terms "first", "second", and the like are used to differentiate a certain component from other components, but the scope of the rights should not be construed to be limited by the terms. For example, a first component may be referred to as a second component, and similarly, the second component may be referred to as the first component. It should be understood that, when it is described that a component is "connected to" the other component, the component may be directly connected to the other component or another component may be present therebetween. In contrast, it should be understood that when it is described that a component is "directly connected to" the other component, another component is not present therebetween. Meanwhile, other expressions describing the relationship between the components, that is, expressions such as "between" and "directly between" or "adjacent to" and "directly adjacent to" should be similarly interpreted.

It is to be understood that the singular expression encompasses a plurality of expressions unless the context clearly dictates otherwise and it should be understood that the term "including" or "having" indicates that a feature, a number, a step, an operation, a component, a part, or the combination thereof described in the specification is present, but does not exclude a possibility of presence or addition of one or more other features, numbers, steps, operations, components, parts or combinations thereof, in advance. Unless otherwise a singular form has a explicitly different meaning contextually, If it is not contrarily defined, all terms used herein have the same meanings as those generally understood by the skilled person in the art. Terms which are defined in a generally used dictionary should be interpreted to have the same meaning as the meaning in the context of the related art, and are not interpreted as an ideal meaning or excessively formal meanings unless clearly defined in the present disclosure.

A device for generating data for art-based psychoanalysis 1 of the present disclosure may improve a compression rate of drawing data to be used for art-based psychoanalysis through encoding and decoding by an autoencoder, and deduce diverse results of art-based psychoanalysis through partial augmentation of drawing data of a partial GAN (generative Adversarial Network). In order to implement this, elements of a system are as follows.

FIG. 1 is a block view schematically showing a device for generating data for art-based psychoanalysis according to one embodiment of the present disclosure.

Referring to FIG. 1, a device for generating data for art-based psychoanalysis 1 is equipped with a user interface 10, a first drawing analysis part 20, a storing part 30 and a second drawing analysis part 40, and this may further be equipped with a psychological state analysis part and a database 60.

The user interface 10 provides an environment where a user 2 can interact with the device for generating data for art-based psychoanalysis 1, and covers a hardware device and a software program for converting a command that was input by the user 2 into electronic data. For example, this may include an input device such as a keyboard, a mouse, a touch pen, etc., an output device such as a display, etc., and a drawing application that processes data such as a contour line, a color, etc. and then displays processed data on an output device in real time.

Further, drawing data is input into the user interface 10 by the user 2, wherein the drawing data of the present disclosure may be a drawing that was drawn by the user and includes an object becoming an art-based psychoanalytic element and an item forming the object. In the present disclosure, the object and item of the drawing data and a method for art-based psychoanalysis for an art-based psychoanalysis service are not limited, however, that method may be a HTP test that analyzes a psychological state of the user from a shape, a color, a location of a drawing following giving the user an assignment to draw a house, a tree and a person. Accordingly, the object of the drawing data may be at least one of those house, tree and person drawn by the user, in which an item forming the house which is an object of the drawing data may include a house outline (a roof, a wall, a chimney, etc.) a window and a door, and an item forming the tree may include a stem, a root, a leaf, a fruit, etc.

The first drawing analysis part 20 analyzes the drawing data that was input through the user interface 10 by user and crops data of a region of interest (ROI) from the drawing data, followed by compressing (encoding) the data of a region of interest or uncompressing compressed data of a region of interest to restore (decoding) the drawing data, wherein this may be subjected to learning using a first artificial intelligence model 21 for performing those encoding and decoding processes.

At this time, the first artificial intelligence model 21 may be an autoencoder for compressing or uncompressing the data of a region of interest through the encoding and decoding processes.

One example of a compression process in which the first drawing analysis part 20 that learned the first artificial intelligence model 21 compresses the data of a region of interest from the drawing data is as follows.

Figure 2:
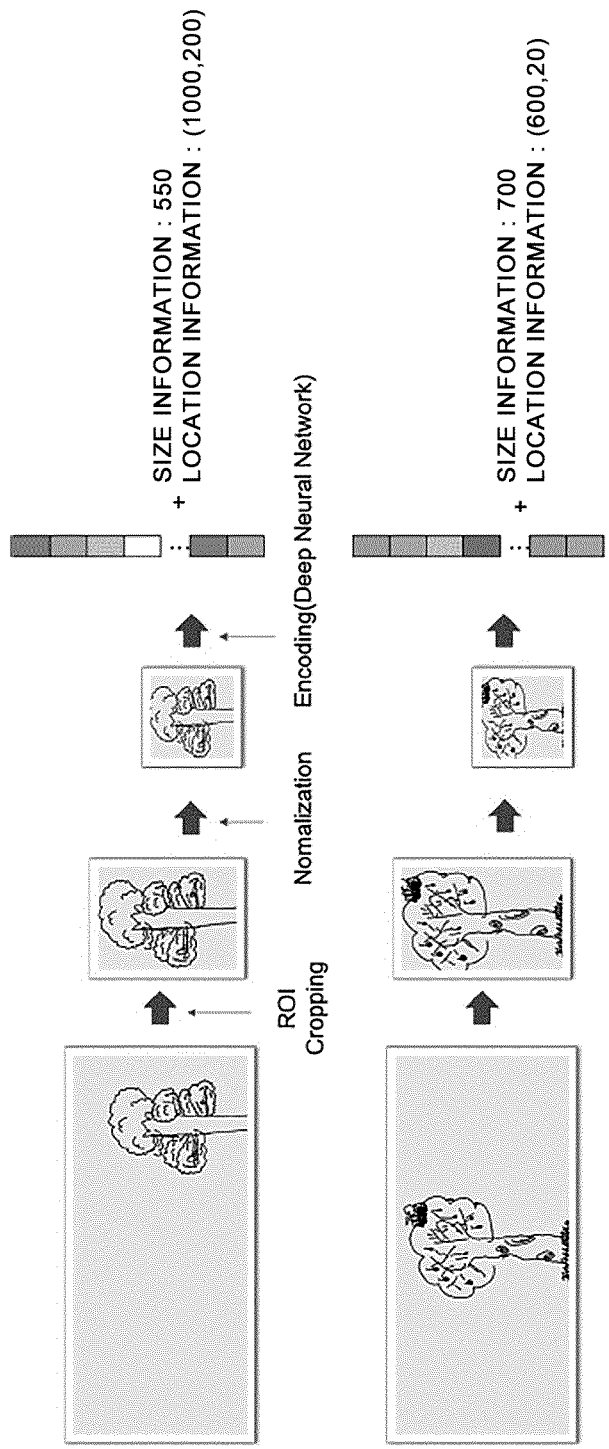
FIG. 2 is a schematic view of one example of a cropping and compression process in which data of a region of interest of a first drawing analysis part as shown in FIG. 1 is cropped and then compressed.
Figure 3:
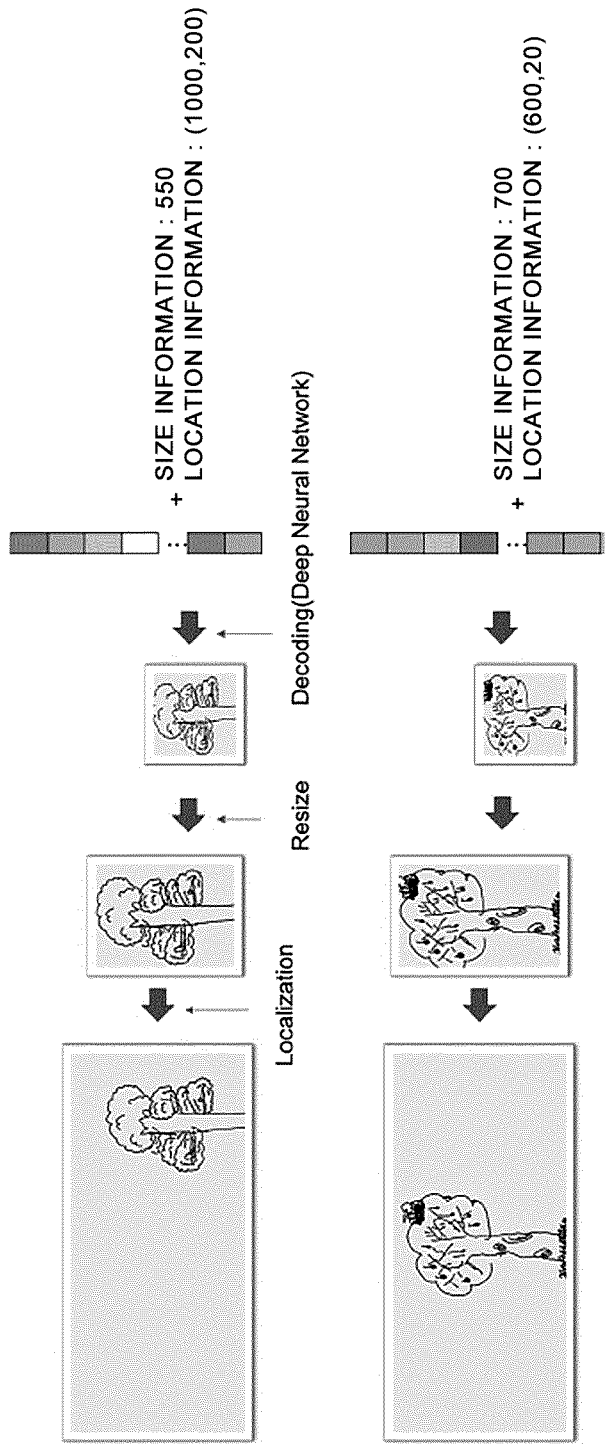
FIG. 3 is a schematic view showing one example of a restoring process in which drawing data of the first drawing analysis part as shown in FIG. 1 is restored.

FIG. 2 is a schematic view of one example of a cropping and compression process in which data of a region of interest of a first drawing analysis part as shown in FIG. 1 is cropped and then compressed. FIG. 3 is a schematic view showing one example of a restoring process in which drawing data of the first drawing analysis part as shown in FIG. 1 is restored.

Referring to FIG. 2, the first drawing analysis part 20 crops data of a region of interest including an object to be used as an evaluation element in art-based psychoanalysis from drawing data that was input into the user interface 10 (referring to 'ROI Cropping' of FIG. 2), followed by normalizing the data of a region of interest into a preset size (referring to 'Normalization' of FIG. 2), and encoding normalized data of a region of interest (referring to 'Encoding' of FIG. 2) to compress feature information. At this time, the feature information refers to labeling information of a size, a location, an angle of the object included in the data of a region of interest to allow learning of the first artificial intelligence model 21, and this signifies attribute (tag) information allowing the first artificial intelligence model 21 to recognize what object is.

The labeling information of the size, location and angle of the object, which was compressed through encoding by the first drawing analysis part 20, may be stored in the storing part 30.

Meanwhile, the drawing data that was input into the user interface 10 may include information of input time of pixels. That is, art-based psychoanalysis according to a prior contactless method does not allow an examiner to observe the moment when an examinee, i.e., the user 2 draws a drawing, in real time, this resulting in difficulties in understanding priority and importance between objects of the drawing data. For example, when drawing a tree, a different result may be deduced depending on the order what is drawn is, such as drawing a stem first and a root later or drawing conversely. When performing remote-art-based psychoanalysis, since it is not able to check the order to draw a drawing, there is a difficulty in accurate analysis.

Accordingly, the device for generating data for art-based psychoanalysis 1 may analyze a psychological state of a user, considering the order to draw objects included in drawing data. For this, the first drawing analysis part 20 determines the order to draw objects and items included in the drawing data received from the user interface 10, storing information of the order in which the objects and items were drawn in the storing part 30 and when the second drawing analysis part 40 generates data for art-based psychoanalysis of the user, making the information of the order in which the user drew the objects and items be included into the data for art-based psychoanalysis of a user, thereby analyzing a psychological state of the user, considering the order in which the objects and items were drawn in the psychological state analysis part 50. At this time, it is preferable to pre-store, in the database 60, the psychological information according to the order to draw objects and items to be transmitted when analyzing the psychological state of the user, so that the psychological state analysis art 50 analyzes the psychological state of the user considering the order in which the objects and items were drawn.

Hereinafter, described are some example of psychoanalysis information according to an order in which a subject, i.e., the user 2 draws a drawing.

Example 1: When instructing a subject to draw family members, in a case that the subject draws a specific family member (particularly, parents) the most lastly, this shows that the subject is more likely to be lacking in an attachment relationship with that family member.

Example 2: When instructing a subject to draw family members including the subject himself/herself, in a case that the subject draws himself/herself the most lastly, this shows that the subject is more likely to be lacking in low self-esteem and self-love.

Example 3: When the subject repeats drawing and erasing a certain object, this shows that the subject is more likely to be lacking in self-confidence and to have a symptom of separation anxiety such as anxiety, compulsion, etc.

According to the aforementioned results, it is able to overcome therapeutic limits resulting from contactless art-based psychoanalysis not allowing real-time observation of such a process in which a subject draws a drawing.

The storing part 30 stores labeling information of a size, a location and an angle of an object, which was compressed through the first drawing analysis part 20 and thus relatively improves a compression rate of the data as compared to storing drawing data that was input into the user interface 10 as it is, thereby efficiently storing the data in a storing part with a limited storage capacity.

This storing part 30 may be either a volatile or non-volatile storing medium installed in the interior of the device for generating data for art-based psychoanalysis 1, or a storing medium present in the exterior of the device for generating data for art-based psychoanalysis 1 and accessible thereto through a network.

The first drawing analysis part 20 is subjected to learning to restore the drawing data through the labeling information of the size, location and angle of the object stored in the storing part 30 during a decoding process of the first artificial intelligence model 21. One example that the first drawing analysis part 20 restores the drawing data through decoding is as follow.

Referring to FIG. 3, the first drawing analysis part 20 restores compression of normalized data of a region of interest by decoding feature information stored in the storing part 30 ('Decoding' of FIG. 3). Once the compression of the data of a region of interest is restored, a size of an object included in the normalized data of a region of interest is regulated through size information stored in the storing part 30 ('Resize' of FIG. 3) to restore the object so as to make the size thereof become the same as that of an object of the drawing data. Once the regulation of the size of the object is completed, a location of the object included in the data of a region of interest normalized through the location information is identified and then the drawing data is restored by regulating the location of the object to the same location as that of the object of the drawing data.

Referring to FIG. 1 again, the second drawing analysis part 40 is subjected to learning with the second artificial intelligence model 41 in order to partially augment an object of a psychoanalytic element included in the data of a region of interest which was uncompressed and then normalized during the decoding process of the first drawing analysis part 30, generating data for art-based psychoanalysis by a combination of objects through the learning the second artificial intelligence model 41.

At this time, the second artificial intelligence model 41 may be a partial GAN for partially augmenting the object included in the normalized data of a region of interest.

Further, a plurality of partial GNAs is equipped in the second drawing analysis part 40 so as to partially augment the object included in the normalized data of a region of interest, and learns feedback on the partial augmentation of the object to generate the data for art-based psychoanalysis. That is, various kinds of data for art-based psychoanalysis may be deduced from a combination of partial GANs.

One example of a learning process of this partial GAN is as follow. In one example hereinafter, the partial GAN is may be formed with a plurality of GANs which separately generate items, such as a house outline, a window and a door, those forming a house that is one among object for a HTP test.

Figure 4:
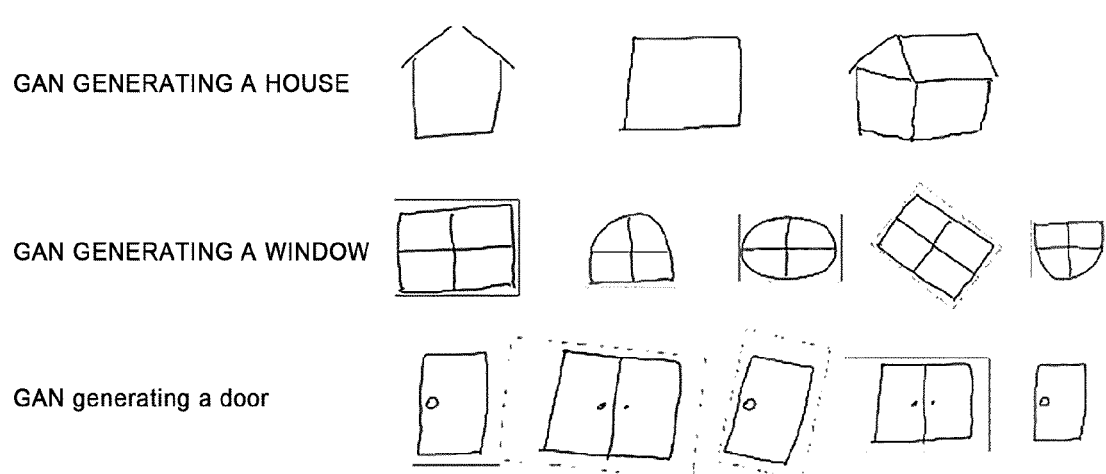
FIG. 4 is a view showing an example of a GAN learning process of a second drawing data analysis part as shown in FIG. 1.
Figure 5:
FIG. 5 is a view showing an example of result data of art-based psychoanalysis generated by a combination of GANs by the second drawing analysis part.

FIG. 4 is a view showing an example of a GAN learning process of a second drawing data analysis part as shown in FIG. 1. FIG. 5 is a view showing an example of result data of art-based psychoanalysis generated by a combination of GANs by the second drawing analysis part.

Referring to FIG. 4, in the second drawing analysis part 40, a partial GAN, i.e., the second artificial intelligence model 41 is formed with GANs generating items of a psychoanalytic element, that is, a GAN generating a house outline, a GAN generating a window and a GAN generating a door. The second drawing analysis part 40 performs learning to generate those house outline, window and door through inputting normalized data of a region of interest.

Referring to FIG. 5, the second drawing analysis part 40 generates diverse cases of houses, such as a house combined with a house outline and a window, one combined with a door and a house outline and one combined with a window and a door and may variously generate data for art-based psychoanalysis relating to the house by performing learning therethrough.

Referring to FIG. 1 again, the psychological state analysis part 50 analyzes data for art-based psychoanalysis generated in the second drawing analysis part 20 and art-based psychoanalytic information pre-stored in the database 60 to firstly deduce a psychological state of the user. For this, the psychological state analysis part 50 is subjected to learning using the third artificial intelligence model 51.

At this time, the third artificial intelligence model 51 signifies a model that is composed of multiple layers and configured to implement a function similar to human's neuro network. An artificial neuro network, such as an RNN (Recurrent Neural Network), a CNN (Convolutional Neural Network), an Attention-based model, etc., is used and the third artificial intelligence model 51 may be learned to deduce the psychological state of the user by performing a search on the art-based psychoanalytic information pre-stored in the database 60.

Further, the psychological state information of the user firstly deduced in the psychological state analysis part 50 is output from a display equipped in the device for generating data for art-based psychoanalysis 1 through the user interface 10 and then may be provided to the user.

Information of art-based psychoanalysis is pre-stored in the database 60. The art-based psychoanalytic information includes what object and item are included when a user draws a drawing, what object and item are drawn largely or small, a psychoanalysis result on whether or not what differences an object and an item have from conventional appearances, accumulated data of contact or contactless psychology consultation, a paper material related to the art-based psychoanalysis, etc. This art-based psychoanalytic information may be updated by a self-result obtained from the device for generating data for art-based psychoanalysis 1.

Hereinafter, taking account of differences of the device for generating data for art-based psychoanalysis 1 according to one embodiment of the present disclosure, a device for generating data for art-based psychoanalysis according to another embodiment of the present disclosure will be described in detail.

Figure 6:
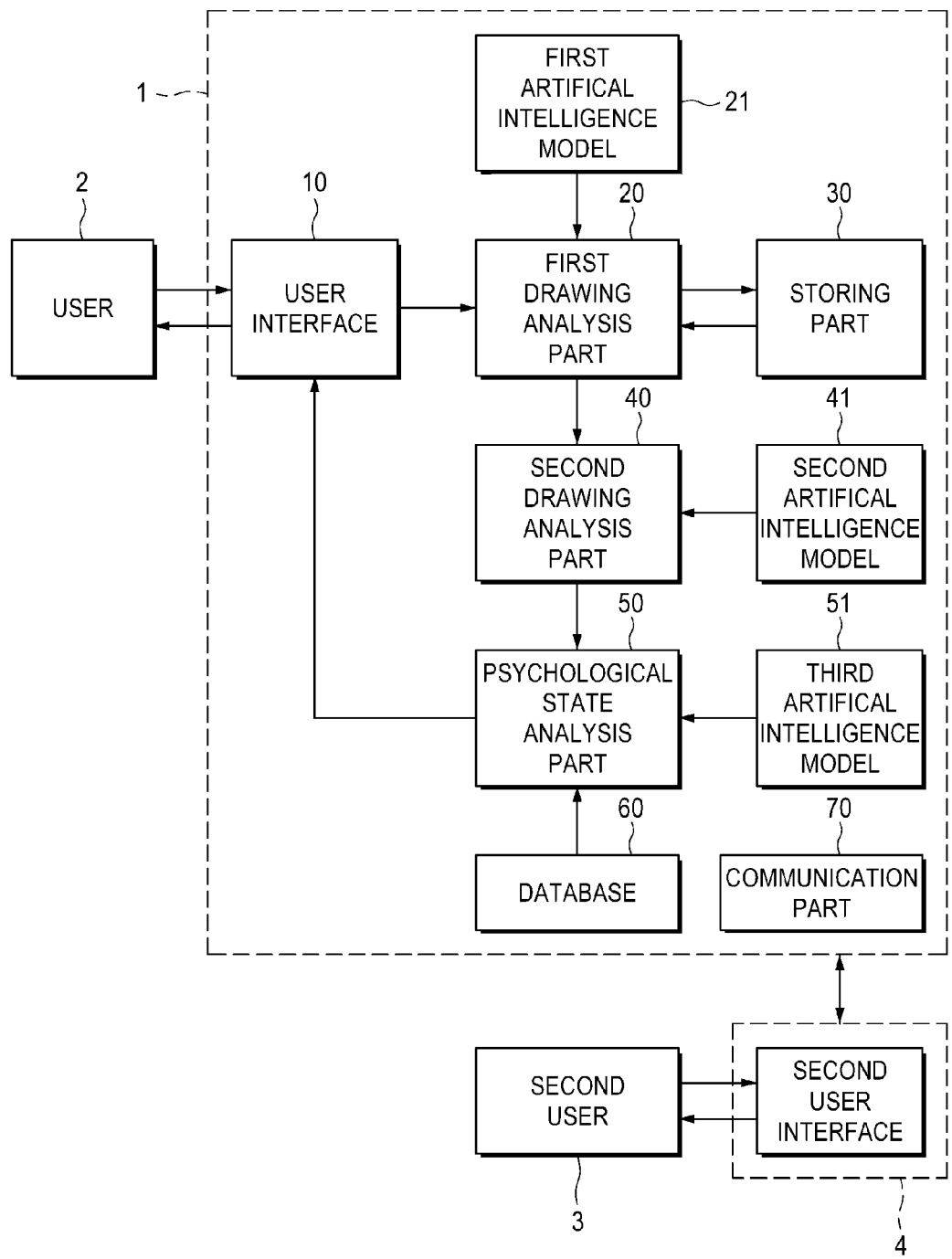
FIG. 6 is a block view schematically showing a device for generating data for art-based psychoanalysis according to another embodiment of the present disclosure.

FIG. 6 a block view schematically showing a device for generating data for art-based psychoanalysis according to another embodiment of the present disclosure.

Referring to FIG. 6, a device for generating data for art-based psychoanalysis 1 according to another embodiment of the present disclosure may further include a communication part 70 for communication of the user 2, that is, a subject with a second user terminal 4 which a second user 3, that is, a drawing analyst has.

The second user terminal 4 may provide the second user 3 with drawing data which the user 2 input into the user interface 10, or be equipped with a second user interface that allows the second user 3 to input additional information including a psychoanalytic opinion deduced by analyzing the drawing data received from the device for generating data for art-based psychoanalysis 1.

When inputting additional information into the second user interface and then receiving the additional information through the communication part 70, the psychological state analysis part 50 adds the additional information to psychological state information of the user firstly deduced through analyzing data for art-based psychoanalysis of the second drawing analysis part 40 and art-based psychoanalytic information pre-stored in the database 60, and this thus may secondly deduce psychological state information of the user.

That is, the secondly deduced psychological state of the user refers one added with the additional information including the opinion on psychoanalysis of the second user 3, and may be psychological state information of the user resulting from changing the firstly deduced psychological state information of the user according to the additional information.

Meanwhile, it is preferable that the device for generating data for art-based psychoanalysis 1 outputs the psychological state of the user which was firstly or secondly deduced by the psychological state analysis part 50, through the user interface 10. However, when outputting the secondary deduced psychological state of the user, this may be controlled to output the firstly deduced psychological state of the user in which no additional information is included, together, thereby providing the user 2, i.e., a subject with diverse psychological states.

Hereinafter, a process in a method for art-based psychoanalysis using a device for generating data for art-based psychoanalysis 1 will be described in detail.

Figure 7:
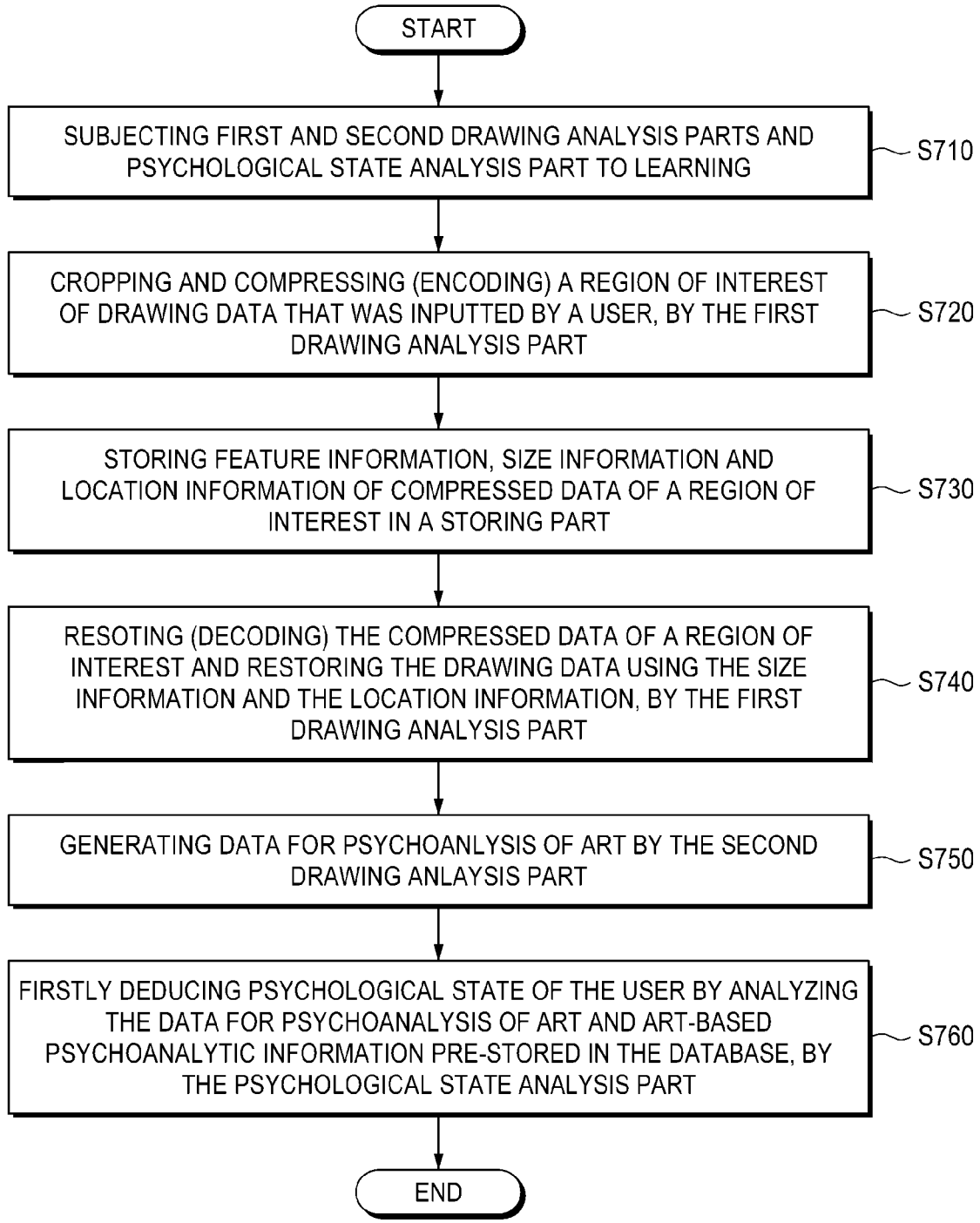
FIG. 7 is a flowchart showing a method for augmentation and efficient management of data for art-based psychoanalysis according to one embodiment of the present disclosure, and FIG. 8 a flowchart showing a method for augmentation and efficient management of data for art-based psychoanalysis according to another embodiment of the present disclosure.

FIG. 7 is a flowchart showing a method for augmentation and efficient management of data for art-based psychoanalysis according to one embodiment of the present disclosure.

Referring to FIG. 7, each of a first drawing analysis part 20, a second drawing analysis part 40 and a psychological state analysis part 50 may be subjected to learning using a first artificial intelligence model 21, a second artificial intelligence model 41 and a third artificial intelligence model 51, respectively S710.

Then, the first drawing analysis part 20 crops data of a region of interest including an object of an art-based psychoanalytic element and an item forming the object from drawing data which a user 2 input through a user interface 10, followed by compressing the data of a region of interest S720 and labeling information of a size, a location and an angle of compressed data of a region of interest may be stored in a storing part 30 S730.

Then, the first drawing analysis part 20 receives feature information from the storing part 30 and uncompresses the compressed data of a region of interest to generate normalized data of a region of interest, thereby restoring the drawing data using size information and location information S740.

Then, the second drawing analysis part 4 that was subjected to learning by partially augmenting the object of the art-based psychoanalytic element included in the drawing data may generate data for art-based psychoanalysis with a combination of the object S750.

Then, the psychological state analysis part 50 analyzes the data for art-based psychoanalysis generated in the second drawing analysis part 40 and art-based psychoanalytic information pre-stored in the database 60, allowing firstly deducing psychological state information of the user S760.

The process of the method for art-based psychoanalysis using a device for generating data for art-based psychoanalysis 1 according to one embodiment of the present disclosure S710 to S760 may be performed by a device for generating data for art-based psychoanalysis 1 described referring to FIG. 5. For the purpose of convenience, since detailed content is the same as that mentioned above, overlapped descriptions will be omitted hereinafter.

Furthermore, the process of the method for art-based psychoanalysis using the device for generating data for art-based psychoanalysis 1 according to one embodiment of the present disclosure may further include secondary deducing psychological state information of the user, and the process is as follows.

Hereinafter, taking account of differences from the method for art-based psychoanalysis using the device for generating data for art-based psychoanalysis 1 according to one embodiment of the present disclosure, a process of a method for art-based psychoanalysis using a device for generating data for art-based psychoanalysis 1 according to another embodiment of the present disclosure will be described in detail.

Further, for the purpose of convenience, since the process of the method for art-based psychoanalysis S810 to S860 is the same as that of the method for art-based psychoanalysis according to one embodiment of the present disclosure but different therefrom only in only reference numbers, a description of that process will be omitted hereinafter.

Figure 8:
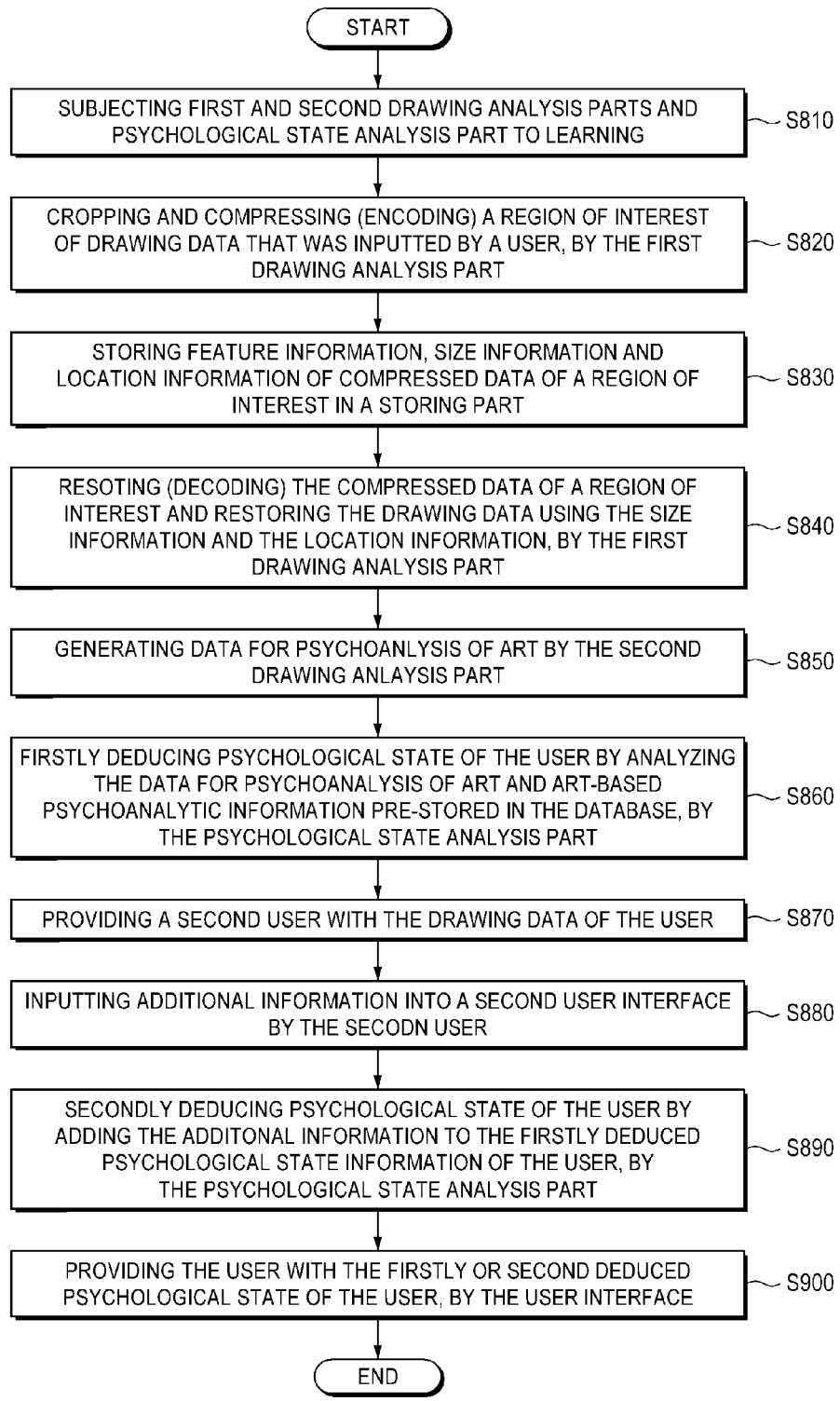

Referring to FIG. 8, following a first deduction of psychological state information of a user, a second user, i.e., a psychoanalyst may receive drawing data of the user from a device for generating data for art-based psychoanalysis through a second user interface equipped in a terminal of the second user and a communication part 70 S870.

Then, the second user analyzes the drawing data of the user, allowing inputting additional information including a psychoanalytic opinion on the drawing data into the second user interface S880.

Then, a psychological state analysis part 50 adds the additional information received from the terminal 4 of the second user through the communication part 70 to the firstly deduced psychological state information of the user, allowing secondly deducing psychological state information of the user S890.

Then, the device for generating data for art-based psychoanalysis 1 may provide the user with the firstly or secondly deduced psychological state information of the user S900. At this time, the device for generating data for art-based psychoanalysis 1 may output the firstly deduced psychological state information of the user and the secondary deduced psychological state information of the user together through controlling a display.

The process of the method for art-based psychoanalysis using the device for generating data for art-based psychoanalysis 1 according to another embodiment of the present disclosure S860 to S900 may be performed by the device for generating data for art-based psychoanalysis 1 as described referring to FIG. 6. For the purpose of convenience, since detailed content is the same as that mentioned above, overlapped descriptions will be omitted hereinafter.

Meanwhile, methods for art-based psychoanalysis using devices for generating data for art-based psychoanalysis 1 according to embodiments of the present disclosure may be implemented into an application, or a program command type that may be performed through various elements of a computer, to be recorded in a computer-readable recording medium. The computer-readable recoding medium may include a program command, a data file, a data configuration, etc. solely, or a combination thereof.

An example of the computer-readable recording medium includes: a magnetic medium such as a hard disk, a floppy disk and a magnetic tape; an optical recording medium such as a CD-ROM and a DVD; a magneto-optical medium such as floptical disk; and a hardware device that is specially configured to store and perform a program command, such as a ROM, a RAM, a flash memory.

Detailed descriptions of the preferred exemplary embodiments of the present disclosure disclosed as described above are provided so as for the skilled person in the art to implement and execute the present disclosure. The present disclosure has been described with reference to the preferred exemplary embodiments, but the skilled person in the art will understand that the present disclosure can be variously modified and changed without departing from the scope of the present disclosure. For example, the skilled person in the art may use the respective components disclosed in the exemplary embodiments by combining the respective components with each other. Therefore, the present disclosure is not limited to the exemplary embodiments described herein, but intends to grant the widest range which is coherent with the principles and new features disclosed herein.

The present disclosure may be embodied in other specific forms without departing from the spirit and essential characteristics of the present disclosure. Accordingly, the aforementioned detailed description should not be construed as restrictive in all terms and should be exemplarily considered. The scope of the present disclosure should be determined by rational construing of the appended claims and all modifications within an equivalent scope of the present disclosure are included in the scope of the present disclosure. The present disclosure is not limited to the exemplary embodiments described herein, but intends to grant the widest range which is coherent with the principles and new features presented herein. Further, the claims that are not expressly cited in the claims are combined to form an exemplary embodiment or be included in a new claim by an amendment after the application.

The invention claimed is:

1. A device for generating data for art-based psychoanalysis, the device comprising:

a user interface that provides a user with an interactive environment;

a first drawing analysis part that is subjected to learning using a first artificial intelligence model, analyzes drawing data that was input through the user interface by the user to crop data of a region of interest from the drawing data, and compresses the data of the region of interest or uncompresses compressed data of the region of interest to restore the drawing data;

a storing part that stores labeling information of a size, a location and an angle of an object included in the compressed data of the region of interest;

a second drawing analysis part that is equipped with a second artificial intelligence model which partially augments an object of an art-based psychoanalytic element included in the drawing data, followed by learning;

a database in which art-based psychoanalytic information is pre-stored;

a psychological state analysis part that is subjected to learning using a third artificial intelligence model and analyzes the data for art-based psychoanalysis and the art-based psychoanalytic information to firstly deduce psychological state information of the user;

a communication part for communicating with a terminal of a second user, wherein the terminal of the second user provides the second user with drawing data input into the user interface by the user, and is equipped with a second user interface so as to input additional information including a psychoanalytic opinion on the drawing data analyzed by the second user, and wherein the psychological state analysis part adds the additional information to the psychological state information of the user firstly deduced through analyzing the data for art-based psychoanalysis and the art-based psychoanalytic information to secondly deduce psychological state information of the user.

2. The device for generating data for art-based psychoanalysis of claim 1, wherein the first artificial intelligence model is an autoencoder for compressing or uncompressing the data of the region of interest.

3. The device for generating data for art-based psychoanalysis of claim 2, wherein the first drawing analysis part crops data of the region of interest from the drawing data, and then normalizes the data of the region of interest into a preset size, followed by encoding normalized data of the region of interest to compress feature information.

4. The device for generating data for art-based psychoanalysis of claim 3, wherein the feature information is labeling information of a size, a location and an angle of an object included in the data of the region of interest.

5. The device for generating data for art-based psychoanalysis of claim 4, wherein the first drawing analysis part decodes the feature information to restore compression of the normalized data of the region of interest, regulates a size of an object included in the normalized data of the region of interest through size information to restore the object so as to make the size thereof become the same as that of an object of the drawing data, and identifies a location of an object included in the normalized data of the region of interest through location information, followed by regulating the location of the object to the same location as that of an object of the drawing data to restore the drawing data.

6. The device for generating data for art-based psychoanalysis of claim 5, wherein the second artificial intelligence model is a partial GAN (Generative Adversarial Network) for partially augmenting an object included in normalized data of the region of interest which is uncompressed through decoding of the feature information.

7. The device for generating data for art-based psychoanalysis of claim 6, wherein a plurality of the partial GANs are equipped in the second drawing analysis part to partially augment the object and subjected to learning through feedback on partial augmentation of the object, and generates data for the art-based psychoanalysis with the partial augmentation of the object.

8. A method for augmentation and efficient management of data for art-based psychoanalysis, the method comprising steps of:

subjecting a first drawing analysis part to learning using a first artificial intelligence model, a second drawing analysis part using a second artificial intelligence part and a psychological state analysis part using a third artificial intelligence model;

cropping data of a region of interest from drawing data that was input through a user interface by a user and compressing the data of the region of interest, by the first drawing analysis part;

storing labeling information of a size, a location and an angle of an object included in the compressed data of the region of interest in a storing part;

uncompressing the compressed data of the region of interest through feature information and then restoring the drawing data, by the first drawing analysis part;

partially augmenting and learning objects of an art-based psychoanalytic element included in the drawing data and generating data for art-based psychoanalysis through a combination of the objects, by the second drawing analysis part;

firstly deducing psychological state information of the user by analyzing the data for the art-based psychoanalysis and art-based psychoanalytic information pre-stored in a database by the psychological state analysis part;

receiving drawing data of the user through a second user interface equipped in a terminal of a second user and a communication part;

inputting additional information including a psychoanalytic opinion on the drawing data into the second user interface, following analyzing the drawing data by the second user;

secondly deducing psychological state information of the user by adding, to the psychological state information of the user deduced by the first psychological state analysis part, the additional information received through the communication part; and providing the user with the firstly or secondly deduced psychological state information of the user through the user interface.

9. A computer program which is stored in a computer-readable recording medium for execution by a computer to perform the method for augmentation and efficient management of data for art-based psychoanalysis of claim 8.

* * * * *